United States Patent [19]

Gamm

[11] Patent Number: 4,570,619
[45] Date of Patent: Feb. 18, 1986

[54] CLAVICLE BRACE

[75] Inventor: Paul B. Gamm, Cincinnati, Ohio

[73] Assignee: Jung Corporation, Cincinnati, Ohio

[21] Appl. No.: 437,108

[22] Filed: Oct. 27, 1982

[51] Int. Cl.[4] ............................................... A61F 5/02
[52] U.S. Cl. .......................................... 128/78; 2/45
[58] Field of Search .................. 128/76, 78, 87 B, 84, 128/DIG. 15, DIG. 19, DIG. 23, 76 R, 87 R; 2/44, 45, 171.2; 119/96; 182/3; 224/905, 911, 153, 160, 204

[56] References Cited

U.S. PATENT DOCUMENTS

| | | | |
|---|---|---|---|
| 84,787 | 12/1868 | Adamson | 128/DIG. 19 |
| 198,504 | 12/1877 | Beauperland . | |
| 531,372 | 12/1894 | Gamble . | |
| 665,688 | 1/1901 | Hollen . | |
| 690,096 | 12/1901 | Bower | 128/78 |
| 714,124 | 11/1902 | Adams | 128/78 |
| 1,050,257 | 1/1913 | Trigg . | |
| 2,450,298 | 9/1948 | Peterson et al. . | |
| 3,141,456 | 7/1964 | Meek | 128/78 |
| 3,307,538 | 3/1967 | Groll | 128/94 |
| 3,338,236 | 8/1967 | McLeod, Jr. . | |
| 3,351,053 | 11/1967 | Stuttle . | |
| 3,382,868 | 5/1968 | Stiefel . | |
| 3,404,680 | 10/1968 | Gutman et al. | 128/94 |
| 3,448,826 | 6/1969 | Rosenblum | 182/3 |
| 3,548,818 | 12/1970 | Kaplan . | |
| 3,718,137 | 2/1973 | Gaylord, Jr. . | |
| 3,856,004 | 12/1974 | Cox | 2/45 |
| 3,857,388 | 12/1974 | Frankel . | |
| 3,897,776 | 8/1975 | Gaylord, Jr. . | |
| 3,906,944 | 9/1975 | Christen | 2/45 |
| 4,198,964 | 4/1980 | Honneffer . | |
| 4,396,091 | 8/1983 | Anderson | 119/96 |

OTHER PUBLICATIONS

Comfort Care Products, Inc. trade literature, p. 11.

Dillon Manufacturing Co., Inc. trade literature, pp. 33 & 34.
Richards Manufacturing Co., Inc. trade literature.

Primary Examiner—Richard J. Apley
Assistant Examiner—S. R. Crow
Attorney, Agent, or Firm—Wood, Herron & Evans

[57] ABSTRACT

A shoulder brace of the type having a generally figure-8 configuration with right and left shoulder loops. Each of the shoulder straps that define the brace's right and left loops are provided with a cushioned inner surface adapted to extend over the wearer's trapezius muscle, over the anterior surface of the wearer's shoulder, and under the wearer's axilla so that the strap does not tend to bite into the wearer's body when the brace is worn. Each shoulder strap also is provided with an adjustable fastener connectable on the anterior surface of the wearer's shoulder between the wearer's trapezius muscle and the wearer's axilla, the fastener permitting the tightness or looseness of the shoulder loop to be adjusted by the wearer as desired while the brace is being worn. Each fastener is in the form of a hook and loop fastener with one of a hook fabric and a loop fabric being fixed to the shoulder strap in a position that overlies the anterior surface of the wearer's shoulder in the before mentioned area when the brace is being worn, and the other of the hook fabric and loop fabric being fixed to the free end of the strap. The free end of the strap is passed through a closed loop link that permits the size of the shoulder loop formed by the strap, and thereby the tightness of the brace on the wearer, to be tightened or loosened simply by drawing the strap through the link in one direction or the other. When the desired tightness of the shoulder loop is achieved, the hook fabric and loop fabric are simply pressed together by the wearer on the anterior surface of the wearer's shoulder.

13 Claims, 4 Drawing Figures

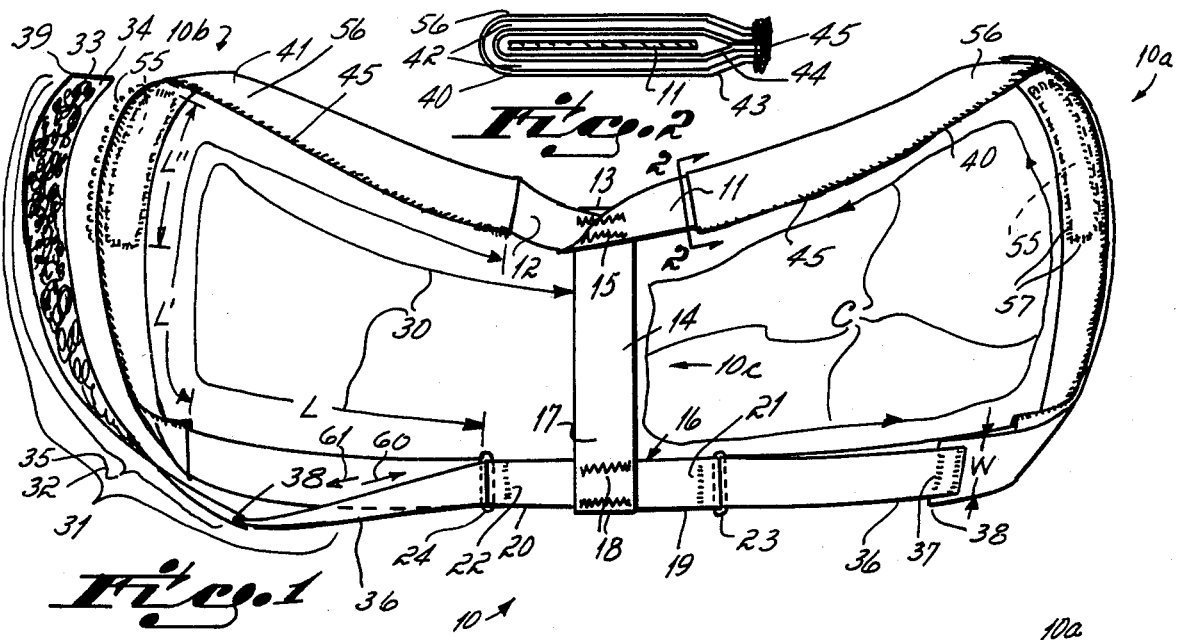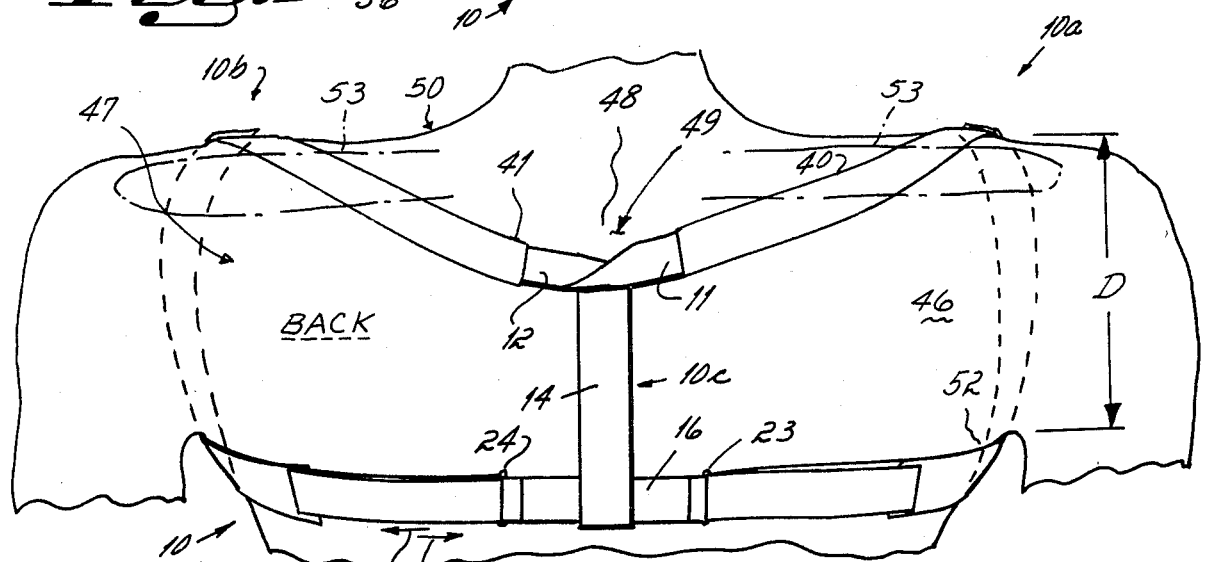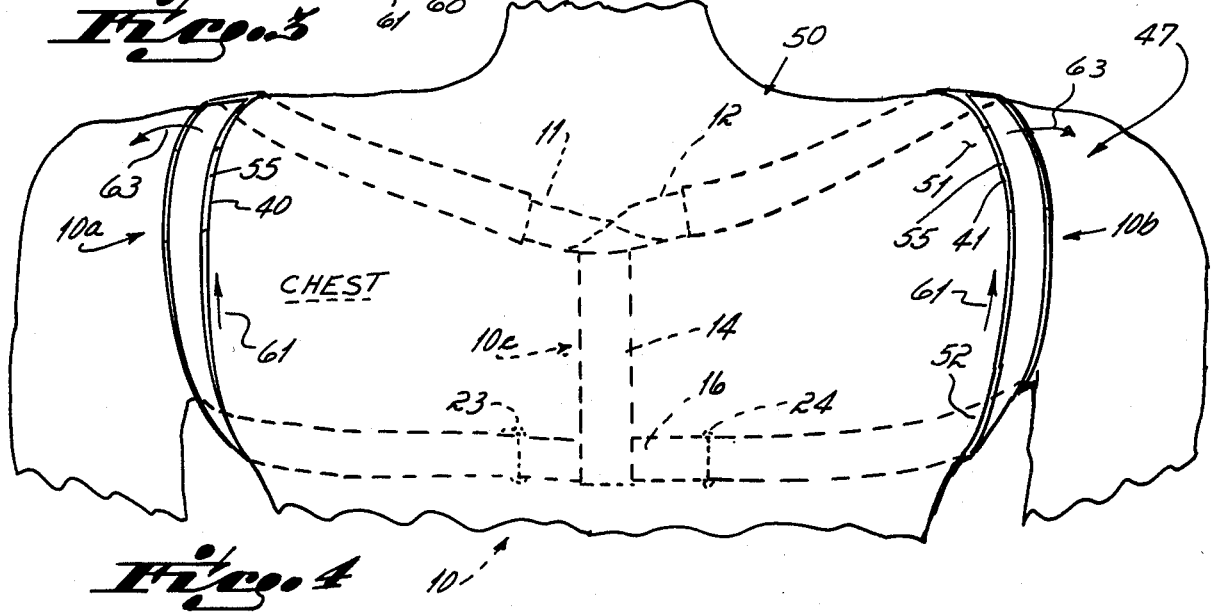

CLAVICLE BRACE

This invention relates to orthopedic type braces. More particularly, this invention relates to a shoulder type orthopedic brace.

Shoulder or clavicle braces are well known in the art. And one type of shoulder or clavicle brace well known in the art is of a generally figure-8 shaped configuration. In this figure-8 type shoulder brace, the crossover location of the brace's right and left shoulder loops overlies the wearer's back, the wearer's arms extending through the shoulder loops when the brace is being worn. This type brace typically includes a pad combined with each strap which overlies the wearer's shoulders, the pad extending under the wearer's axilla so as to tend to minimize biting or discomfort of the straps against the wearer's torso when the brace is being worn. In figure-8 type shoulder braces, it is important that the shoulder straps be provided with an adjustable fastener by which the loops can be increased or decreased in size. This allows the brace to be sized initially depending on the upper body size of the wearer, and also allows the shoulder loops to be tightened or loosened after the brace has been installed on the wearer as required or desired by the wearer and/or attending physician. Typically, each such adjustable fastener is in the form of a buckle that cooperates with the free end of its associated shoulder strap, the buckle being connected to the brace in the center of the wearer's back when the brace is being worn. Indeed, and to the best of my knowledge, all fasteners by which a figure-8 type shoulder brace's shoulder straps are adjustably lengthened or shortened involves some kind of fastener device that, after the brace is installed on the wearer, is located in or closely adjacent to the center of the wearer's back.

The location of shoulder strap fasteners in the middle of a wearer's back when a figure-8 type shoulder brace is being worn results in a significant practical disadvantage to the wearer. This location of the strap fasteners requires that a second person must stand behind the wearer to initially adjust the shoulder strap length to a desired beginning length if such is to be achieved when the brace is in place, and also requires that a second person stand in back of the wearer to subsequently adjust the tightness or looseness of the shoulder straps as the brace is worn during everyday life by the wearer. In other words, the wearer himself cannot initially set the length of the shoulder straps in a final desired or required position while wearing the prior art figure-8 type shoulder braces, and the wearer himself cannot adjust the tightness or looseness of the shoulder straps on that type brace as the brace becomes tighter or looser while being worn during everyday life. Obviously this is a disadvantage of substantial significance to wearers of prior art shoulder braces when no second person is around to help with desired shoulder strap adjustments. In other words, and with the figure-8 type braces of the prior art, to the best of my knowledge none can be adjusted by the wearer himself while the shoulder brace is being worn.

Another disadvantage of the figure-8 type shoulder braces of the prior art is that one end of each shoulder strap is disconnectable from the brace itself in prior art braces. Such is normally disconnectable either for the purpose of making it easier to put the brace on and to take it off, and/or for the purpose of adjusting the length of the shoulder straps when the brace is on or off from a tightness/looseness comfortability standpoint. But when the free ends of a brace's shoulder straps are disconnected from the figure-8 loop configuration defined by the brace, it is possible that when same are reconnected the shoulder straps will be twisted out of the preferred figure-8 loop configuration in some way or another. This twisting of the shoulder straps leads to discomfort to the wearer if the brace is put on, and then tightened in place, with the straps in a twisted configuration.

A further disadvantage of figure-8 type shoulder braces of the prior art is based on the fact that, to the best of my knowledge, same are always made of non-elastic material. In other words, the figure-8 harness that defines the shoulder brace is non-elastic throughout its structure. When this completely non-elastic figure-8 type shoulder brace is worn as a posture aid only, and when the wearer attempts to reach out in front of himself, i.e., to move his shoulder forward by itself, toward an object with his right or left hand, he is most definitely prevented from doing so by the non-elastic nature of the brace. This periodically results in an unnecessary discomfort to the wearer when the purpose of wearing the brace in the first place is only for enhancing the wearer's posture, as opposed to insuring alignment of the wearer's broken clavicle bone, i.e., even though the purpose of wearing the brace does not require that such momentary forward reaching be prevented at all times.

Accordingly, it has been one objective of this invention to provide an improved figure-8 type shoulder brace in which the brace's shoulder straps are adjustable as to length, each of the fasteners by which the shoulder straps are lengthened or shortened being positioned to overlie the anterior surface of one of the wearer's shoulders between the wearer's trapezius muscle and the wearer's axilla when the brace is being worn, thereby allowing the wearer himself to adjust the length of the brace's shoulder straps without requiring the help of a second person for both initially setting the desired tightness of the brace, as well as for subsequently tightening and/or loosening of the brace as desired.

It has been another objective of this invention to provide an improved figure-8 type shoulder brace in which each shoulder strap is adjustable in length for allowing the wearer himself to tighten or loosen the strap when the brace is being worn, each loop of the figure-8 configured brace having a stop on the strap that cooperates with a closed loop link, the stop being located on the strap at such distance from the strap's free end that permits easy adjustment of the strap to provide different sizes for the loop yet prevents the strap from being withdrawn from threaded assembly with that link during normal use, thereby preventing the strap from being twisted relative to the closed loop link which might otherwise occur if one section of the strap was periodically disconnected from another section of the shoulder strap, i.e., if the loop was periodically broken.

It has been a further objective of this invention to provide an improved figure-8 type shoulder brace in which each shoulder loop defined by a shoulder strap is provided with an elastic section, the elastic section having a degree of elasticity of such strength that the wearer's shoulder is normally held in position as set by the figure-8 loop harness when the brace is worn, but which is not of such strength that the wearer cannot momentarily exceed the strength level required to slightly stretch that elastic section without discomfort being experienced by the wearer when reaching forwardly to an object in front of the wearer, the elastic section returning to its set position when the wearer's shoulder action again reduces to below the strength level required for stretching the elastic section.

In accord with these principles and objectives, the figure-8 type shoulder brace of this invention includes right and left shoulder loops. Each of the shoulder straps that define the brace's right and left loop is provided with a cushioned inner surface adapted to extend over the wearer's trapezius muscle, over the anterior surface of the wearer's shoulder, and under the wearer's axilla so that the strap does not tend to bite into the wearer's body when the brace is worn. Each shoulder strap also is provided with an adjustable fastener connectable on the anterior surface of the wearer's shoulder between the wearer's trapezius muscle and the wearer's axilla, the fastener permitting the tightness or looseness of the shoulder loop to be adjusted by the wearer as desired while the brace is being worn. Each fastener is in the form of a hook and loop fastener with one of a hook fabric and a loop fabric being fixed to the shoulder strap in a position that overlies the anterior surface of the wearer's shoulder in the before mentioned area when the brace is being worn, and the other of the hook fabric and loop fabric being fixed to the free end of the strap. The free end of the strap is passed through a closed loop link that permits the size of the shoulder loop form d by the strap, and thereby the tightness of the brace on the wearer, to be tightened or loosened simply by drawing the strap through the link in one direction or the other. When the desired tightness of the shoulder loop is achieved, the hook fabric and loop fabric are simply pressed together by the wearer on the anterior surface of the wearer's shoulder. The free end of each shoulder strap, in one preferred form, also includes a stop fixed to the strap that cooperate with the closed link to prevent the brace's loop defined by that strap from becoming disconnected or broken or opened. The stop is positioned from the strap's terminal end a distance sufficient to maintain the desired degree of length adjustability in the strap as established by the strap's adjustable fastener. Further, and in another preferred form, each shoulder loop includes an elastic section of such strength as to normally prevent stretching thereof during most everyday activities of the wearer. Yet the elastic section's strength is such that it may be momentarily exceeded if the brace's wearer reaches outwardly in front of himself by moving his arm and shoulder relative to his upper body. This elastic section promotes the wearer's comfort as the brace is worn during everyday life when the brace is worn as a posture aid only. The elastic section is not usually incorporated in the brace when the brace is worn as a surgical brace for a broken clavicle bone as in that circumstance no such forward motion ordinarily is permissible.

Other objectives and advantages of this invention will be more apparent in the following detailed description taken in conjunction with the drawings in which:

FIG. 1 is a rear perspective view of a figure 8 type clavicle brace in accord with the principles of this invention;

FIG. 2 is a cross-sectional view taken on line 2—2 of FIG. 1;

FIG. 3 is a rear view similar to FIG. 1, the brace being in position; and

FIG. 4 is a front view of the brace, as seen in position.

A shoulder brace 10 in accord with the principles of this invention is illustrated in FIG. 1. As shown, same is of a generally figure 8 type having a right shoulder loop 10a and a left shoulder loop 10b, the loops being connected together one with the other at the figure 8 crossover 10c. The brace 10 basically includes a non-elastic right shoulder strap 11 of adjustable length and a non-elastic left shoulder strap 12 of adjustable length, these straps being fixedly and immobily connected to top end 13 of a non-elastic center strap 14 by stitch lines 15. An elastic cross strap 16 is connected to bottom end 17 of the non-elastic center or crossover strap 14 by stitch lines 18. A non-elastic cross strap (not shown) may be substituted for the elastic cross trap 16 if the brace is to be used solely as a surgical brace for a wearer's broken clavicle bone. The ends 19, 20 of the elastic cross strap 16 are each looped over and stitched by stitch lines 21, 22 to closed loop metal links 23, 24, respectively. The links 23, 24 cooperate with the respective shoulder straps 11, 12 to provide adjustability in the bracing length L of the shoulder strap and, therefor, the size of shoulder loops 10a, 10b. Adjustment of each shoulder strap's bracing length L (and, therefor, the size of shoulder loops 10a, 10b) adjusts the tightness or looseness of the brace 10 when same is worn by a user.

Each of the right 11 and left 12 shoulder straps is fabricated from an elongated one piece length of non-elastic webbing. Each of the shoulder straps 11, 12 is comprised of a shoulder contact section 30 and a doubled back section 31, these two sections being of variable length relative one to the other to permit lengthening or shortening the shoulder strap, i.e., the shoulder contact section, as desired for tightening or loosening the brace on the wearer. Outer or free end 32 of each doubled back section 31 terminates in a non-elastic section with a loop pile 33 on the inside surface 34 thereof. The loop pile 33 constitutes the loop portion of a hook and loop type fastener, e.g., a Velcro fastener. More specifically, the free end portion 32 of the doubled back section 31 of the shoulder strap 11, 12 is provided with a non-elastic loop pile web 35 which is fixed to the inner end portion 36 of doubled back web section 31 by stitch line 37. As is particularly apparent in FIG. 1, the width W of the non-elastic loop pile web 35 at the end where same is sewn to the portion 36 of the strap's doubled back section 31, and the position of stitch line 37 by which same is sewn to that section, are located to provide a small flap 38 which cooperates with the closed loop link 23 or 24 through which the shoulder strap section 30 or 31 is threaded. The small flap 38 functions to prevent the free end portion 32 of the strap 11 or 12 from being removed from threaded relation with that link 23, 24 during normal use conditions. In other words, the width W of the non-elastic loop pile web 35 at the flap 38 where the web 35 is stitched to the inner end portion 36 of the doubled back section 31 functions as a stop to prevent the shoulder strap 11 or 12 from being unthreaded with the closed loop link 23 or 24. In this regard, note the stop flap 38 is located at a position substantially removed from terminal end 39 of the strap 11, 12, which position is preferably between about 15% and about 50% of the circumferential length C of the shoulder loop 10a, 10b as established when the flap stop 38 abuts the link 23, 24 (i.e., when the shoulder loop 10a, 10b is extended to its maximum size). These stop flaps 38 provide a distinct advantage in that they cause the shoulder straps 11, 12 to remain always in closed loop 10a, 10b configuration, and since the shoulder straps 11, 12 cannot be unthreaded or separated or disconnected from that closed loop configuration (i.e., from the link 23, 24) under normal use conditions, it can not be rethreaded incorrectly with the link by the wearer.

Each shoulder strap 11, 12 of the figure 8 type shoulder brace 10 also includes a padded sleeve 40, 41 fixed to that strap. As shown in FIG. 2, each padded sleeve 40, 41 is formed from a laminate having a latex foam 42 interior, and outside 43 and inside 44 fabric surfaces. This laminate is initially made in sheet form, the sheet then being folded over the strap 11 or 12, and the sheets' edges fixed one to the other by stitch line 45, to establish the tunnel or sleeve configuration. Each shoulder strap 11, 12 is threaded through its respective padded sleeve 40, 41. Each padded sleeve 40, 41 is of a length L', and is positioned on its respective shoulder strap 11, 12, so that, when the brace is worn by a user, the padded sleeve extends from the posterior surface 46 of the wearer's shoulder 47 (and, preferably, close to the spline area 48 of the wearer's upper back 49), over the wearer's trapezius muscle 50, down over the anterior surface 51 of the wearer's shoulder, through the wearer's axilla 52, and back onto the posterior surface of the wearer's upper back just beyond the axilla. As the padded sleeves 40, 41 so traverse the wearer's shoulders 47, same also traverse the wearer's clavicle 53. The purpose of the padded sleeves 40, 41 is to prevent discomfort to the wearer which might otherwise occur by virtue of the shoulder straps 11, 12 biting into the wearer's trapezius muscle 50 or axilla 52 or shoulder flesh when the brace is being worn and is drawn tight on the wearer's shoulder 47.

A non-elastic hook fabric path 55 is fixed to each shoulder strap 11, 12 on exterior surface 56 of the padded sleeve 40, 41, the stitch lines 57 being shown in FIG. 1. The hook fabric patch 55 preferably is of a length L" no greater than the distance D between the brace wearer's trapezius muscle 50 and axilla 52. The hook fabric of the patch 55 constitutes the hook portion of a hook and loop type fastener, e.g., a Velcro fastener. The stitching or sewing of the hook fabric patch 55 to its respective shoulder strap 11, 12 not only serves to connect the hook fabric patch to the shoulder strap, but also serves to fixedly connect the respective padded sleeve 40, 41 to the shoulder strap. In other words, stitch lines 57 for patch 55 also serve to stitch padded sleeve 40, 41 in the desired fixed position on shoulder strap 11, 12. Importantly relative to the principles of this invention, and as shown in FIG. 4, the hook fabric patch 55 is fixed to each shoulder strap 11, 12, and is of such length L", that it will overlie the anterior surface 51 of a wearer's shoulder 47 between the wearer's axilla 52 and the wearer's trapezius muscle 50 when the brace 10 is being worn by the wearer. Preferably, the hook fabric patch 55 is secured to shoulder strap 11, 12 at such a position, and is of such a length L", that it traverses the wearer's clavicle 53 when the brace is being worn. It will be understood to those skilled in the art that the non-elastic hook fabric path 55 and the non-elastic loop pile web 35 constitute a type of fastener by which the free end portion 32 of the doubled back section 31 of the shoulder strap 11, 12 can be fastened or connected to the shoulder contact section 30 of the shoulder strap at any desired and/or required position simply by pressing the loop pile web 35 against the hook fabric path 55.

Use of the shoulder or clavicle brace 10 of this invention is as illustrated in FIGS. 3 and 4. Initially, and prior to the brace 10 being installed on the wearer, each of the right 10a and left 10b shoulder loops are expanded to maximum loop size simply by disconnecting each strap's loop pile web 35 from each strap's hook fabric path 55, and then drawing the shoulder straps in the direction shown by arrow 60 until flap stops 38 abut closed loop links 23, 24. With the shoulder loops 10a, 10b in the most expanded condition, each loop pile web 35 is then reattached to its respective hook fabric patch 55, and the user then puts on the brace as though he were putting on a jacket.

After the wearer has put on the brace 10 as shown in FIGS. 3 and 4, and to tighten the right shoulder loop 10, with his left hand the wearer himself can then detach, i.e., peel off, the right shoulder loop's loop pile web 35 from the right shoulder loop's hook patch 55. The wearer himself then pulls the shoulder strap's doubled back section 31 in the direction shown by phantom arrow 61 until (which direction includes forward and upward directional components) sam is drawn to the tightness desired or required. This pulling action provides a simultaneous tightening of the right shoulder loop 10a on the wearer's right shoulder, as well an inherent rearward thrust to the wearer's right shoulder for pulling the shoulder rearwardly into the brace position that is desired. Thereafter the wearer's left hand simply presses the right shoulder loop's loop pile web 35 against the right shoulder loop's hook patch 55 so that a positive connection is achieved, i.e., so that the right shoulder loop's doubled back section 31 is fastened to that loop's shoulder contact section 30. Also, and similarly, the brace's left shoulder loop 10b can be tightened by the wearer himself by use of the wearer's right hand. The wearer simply detaches or pulls off the left shoulder loop's loop pile web 35 from the left shoulder loop's hook patch 55 with his right hand, and then draws the left shoulder loop's shoulder contact section 30 tight against his left shoulder 47 by pulling the shoulder strap's doubled back section 31 in the direction shown by arrow 61. (which direction also includes forward and upward directional components). This pulling action provides a simultaneous tightening of the left shoulder loop 10b on the wearer's left shoulder, as well as inherent rearward thrust to the wearer's left shoulder for pulling that shoulder rearwardly into the braced position that is desired. When the degree of thickness desired and/or required is achieved, the wearer's right hand simply depresses the left shoulder loop's loop pile web 35 against the left shoulder loop's hook patch 55, thereby providing a good connection to hold the dimensions of the left shoulder loop 10b stable as the brace is worn. Of course, and at any time while the brace is being worn, the tightness or looseness of either the right 10a or left 10b shoulder loop can be easily varied as desired by the wearer. Such is achieved simply by disconnecting the respective shoulder loop's loop pile web 35 from that shoulder loop's hook patch 55 as by peeling it off in the direction shown by directional arrow 63, thereafter increasing or decreasing the length of the shoulder contact section 30 of the shoulder strap 11, 12 by drawing the strap's doubled back section 31 one way 60 or the other way 61 through link 23, 24, and thereafter reattaching the hook and loop fastener 35, 55 in the manner before mentioned.

The location of the hook patch 55 on the shoulder contact section 30 of each shoulder loop 10a, 10b, same being in front of the wearer and readily accessible to the wearer's hands, permits the objectives and advantages of this invention to be obtained. In other words, since the hook loop patch 55 is located on the anterior surface 51 of the wearer's shoulder 47 between the wearer's axilla 52 and the wearer's trapezius muscle 50 when the brace 10 is being worn by the wearer, and since the length of the doubled back section 31 of the shoulder strap 11, 12 is such that the loop pile web 35 is engageable with the hook patch 55, this permits the wearer himself to initially size, and to at any time thereafter tighten or loosen, the shoulder loops 10a, 10b of the brace while it is being worn.

A further important advantage of this invention is that, as previously mentioned, neither shoulder strap 11, 12 can be disconnected from its closed loop configuration during normal use. This for the reason that flap stop 38 intermediate the ends of the doubled back section 31 of each shoulder strap 11, 12 prevents disconnection or unthreading of the shoulder strap from the closed loop link 23, 24. This, in turn, prevents shoulder strap 11, 12 from being inadvertently and improperly twisted upon being rethreaded with that link 23, 24 since it cannot be unthreaded therefrom in the first place. If shoulder strap 11, 12 were to be inadvertently twisted, such could lead to discomfort for the brace's wearer when the shoulder loops 10a, 10b are drawn tight against the wearer's shoulders 47.

A further objective of this invention is provided by the elastic cross strap 16 to which the brace's links 23, 24 and vertical back strap 14 are connected, thereby providing an elastic section that is part of each shoulder loop 10a, 10b. The elastic cross strap 16 preferably does not stretch until exposed to a stretch force of at least about 100 oz. at 25% stretch of the elastic strap and, most preferably at least about 150 oz. at a 25% stretch of the elastic strap. When the brace 10 is being worn, and when the wearer is engaging in normal every day activities, it becomes uncomfortable at times if the wearer wishes to reach forwardly with his right or left arm in that such forward reaching motion (in which the wearer's shoulder tends to move slightly forward of the wearer's upper body) definitely would be impeded by the brace itself if no such elastic strap 16 were used. But the elastic strap 16, when the stretch force necessary to stretch same is exceeded, allows the wearer's shoulder to move forward relative to the wearer's upper body a limited distance and this in turn aids to the comfort of the wearer while wearing the brace 10. Of course, as soon as the wearer returns his arm and shoulder to the desirable and brace pre-set position, the stretch force is reduced beneath that needed to stretch the elastic strap 16 and the elastic strap returns back to the normal unstretched brace position. This elastic strap 16, therefore, simply serves to allow a little more comfort to the brace's wearer when he attempts to move either his right or left shoulder forward relative to his upper body as might occur in an outward reaching type motion, but serves to remind the wearer that the shoulders must be maintained in alignment as dictated by the brace once the desirability of exceeding that momentary elastic stretch value has been eliminated. The elastic strap 16, with its attendant advantages, normally is used when the brace is primarily intended for use as a posture aid, i.e., to enhance the wearer's posture. The elastic strap 16 normally is not used when the brace is primarily intended for use as a surgical brace for holding the wearer's broken clavicle bone, even limited forward movement of the wearer's shoulder often not being desirable when the clavicle bone is broken.

Having described in detail the preferred embodiment of my invention, what I desire to claim and protect by Letters Patent is:

1. A shoulder brace for bracing a wearer's shoulders, said brace being of the type having a generally figure 8 configuration with right and left shoulder loops connected together to form said figure 8 configuration, the wearer's right and left arms being received through said right and left shoulder loops, respectively, when said brace is worn, said brace comprising a first shoulder strap that defines one of said brace's shoulder loops, and a second shoulder strap that defines the other of said shoulder loops, each of said straps having a shoulder contact section and a doubled back section, each strap's shoulder contact and doubled back sections being connected one to the other, and said doubled back section of each strap being adapted to overlie its associated shoulder contact section on the anterior surface of a wearer's shoulder between the wearer's trapezius muscle and the wearer's axilla when said brace is worn, a crossover strap connected to said first and second shoulder straps for maintaining said first and second shoulder straps in said generally figure 8 configuration, a link fixed to said brace with said shoulder straps being slidable relative to said link for increasing or decreasing the size of said shoulder loops, the tightness or looseness of said brace on a wearer's shoulders being a result of the decreased size or increased size, respectively, of said shoulder loops, and an adjustable fastener connected with each of said first and second shoulder straps, each fastener being partially carried by a shoulder contact section and partially carried by a doubled back section, said fasteners being connectable on the anterior surfaces of the wearer's shoulders between the wearer's trapezius muscle and the wearer's axilla, said fastener associated with said right shoulder loop being adjustable to permit the size of said right loop to be decreased personally by the wearer by pulling said right loop's doubled back section in a direction that includes a forward directional component with the wearer's left hand as desired while the brace is being worn, and said fastener associated with said left shoulder loop being adjustable to permit the size of said left loop to be decreased personally by the wearer by pulling said left loop's doubled back section in a direction that includes a forward directional component with the wearer's right hand as desired while the brace is being worn, the pulling of each loop's doubled back section in a direction that includes a forward directional component simultaneously tightening that loop on the wearer's shoulder and providing a rearward thrust to the wearer's shoulder for pulling the wearer's shoulder rearwardly into a desired braced position.

2. A brace as set forth in claim 1, said fasteners being of the hook and loop type, each of said fasteners comprising one of a hook fabric and a loop fabric fixed to a shoulder contact section in a position that overlies the anterior surface of the wearer's shoulder between the wearer's trapezius muscle and the wearer's axilla when the brace is being worn, and the other of said hook fabric and said loop fabric being fixed to said shoulder strap's doubled back section.

3. A brace as set forth in claim 2, each doubled back section having a free end portion and an inner end portion, said brace further comprising
a stop flap established by the stitching of said free end portion to said inner end portion of each doubled back section, said stop flaps cooperating with said link to maintain said shoulder straps in closed loop configuration, and therefore said brace in said figure 8 configuration, when said fasteners are fastened as well as when said fasteners are unfastened.

4. A brace as set forth in claim 1, said link being fixed to said brace so that said link is positioned adjacent the middle of a wearer's back when said brace is worn.

5. A brace as set forth in claim 1, each of said first and second shoulder straps comprising
a stop connected to said shoulder strap's doubled back section, said stop cooperating with said link to maintain said shoulder strap in closed loop configuration, and therefore said brace in figure 8 configuration, when said fastener is fastened as well as when it is unfastened.

6. A brace as set forth in claim 1, said brace comprising
an elastic section interposed within said shoulder strap structure, said elastic section being of a strength to prevent stretching thereof during normal wear of said brace, but permittng limited stretching thereof when the wearer's shoulder moves slightly forward relative to his upper body.

7. A brace as set forth in claim 6, said link being connected to said elastic section.

8. A brace as set forth in claim 1, each of said first and second shoulder straps comprising
a padded sleeve that surrounds said shoulder strap's shoulder contact section, each shoulder strap extending from the posterior surface of the wearer's upper back, over the wearer's trapezius muscle, over the anterior surface of the wearer's shoulder, through the wearer's axilla and back onto the posterior surface of the wearer's back, when said brace is being worn.

9. A brace as set forth in claim 2, each of said first and second shoulder straps comprising
a padded sleeve that surrounds said shoulder strap's shoulder contact section, each shoulder strap extending from the posterior surface of the wearer's upper back, over the wearer's trapezius muscle, over the anterior surface of the wearer's shoulder, through the wearer's axilla, and back onto the posterior surface of the wearer's back, when said brace is being worn,
said one of said hook and loop fabric being in the form of a patch fixed to the exterior surface of each padded sleeve, and each shoulder strap's doubled back section overlying its associated shoulder contact section, said padded sleeve and said patch when said brace is being worn.

10. A brace as set forth in claim 9, each of said first and second shoulder loops comprising
stitch lines by which each patch is fixed to the exterior surface of its associated padded sleeve, said stitch lines also fixing said padded sleeve to its associated shoulder contact section.

11. A brace as set forth in claim 9, said link being located so that same is positioned on the posterior surface of the wearer's back when said brace is being worn.

12. A method of bracing a person's shoulders through use of a shoulder brace of the type having a generally figure-8 configuration, said method comprising the steps of
providing a pair of shoulder straps that each defines a shoulder loop, said shoulder straps being connected by a crossover strap into said generally figure 8 configuration, each strap having a shoulder contact section and a doubled back section connected one to the other, and that are movable relative one to the other, so that the size of said shoulder loops can be increased or decreased and, thereby, so that the tightness or looseness of the brace on a wearer's shoulders can be varied,
positioning an adjustable fastener on each shoulder strap so that said fastener is connectable on the anterior surface of said wearer's shoulder between the wearer's trapezius muscle and the wearer's axilla, said fastener being partially carried by said shoulder strap's shoulder contact section and partially carried by said shoulder strap's doubled back section,
when said shoulder strap defines a left shoulder loop, and when said brace is being worn, tightening said shoulder loop by said wearer through use of said wearer's right hand pulling said left loop's doubled back section in a direction that includes a forward directional component, and
when said shoulder strap defines a right shoulder loop, and when said brace is being worn, tightening said shoulder loop by said wearer through use of said wearer's left hand pulling said right loop's doubled back section in a direction that includes a forward directional component,
the pulling of each loop's doubled back section in a direction that includes a forward directional component simultaneously tightening that loop on the wearer's shoulder, and providing a rearward thrust to the wearer's shoulder for pulling the wearer's shoulder rearwardly into a desired braced position.

13. A method as set forth in claim 12, said method comprising the further steps of
establishing said adjustable fastener through use of a hook and loop type fastener, and
when said brace is being worn, separating said hook and loop components one from the other, thereafter extending or retracting the length of said shoulder strap's shoulder contact section, and thereafter rejoining said hook and loop components one with another, all with use of one of said wearer's right hand and said wearer's left hand as required.

* * * * *